(12) United States Patent
Tanaka et al.

(10) Patent No.: US 8,709,512 B2
(45) Date of Patent: Apr. 29, 2014

(54) METHOD FOR TREATING HYPERGLYCEMIA

(71) Applicant: Morinaga Milk Industry Co., Ltd., Tokyo (JP)

(72) Inventors: Miyuki Tanaka, Zama (JP); Muneo Yamada, Zama (JP)

(73) Assignee: Morinaga Milk Industry Co., Ltd., Tokyo (JP)

( * ) Notice: Subject to any disclaimer, the term of this patent is extended or adjusted under 35 U.S.C. 154(b) by 0 days.

(21) Appl. No.: 13/680,658

(22) Filed: Nov. 19, 2012

(65) Prior Publication Data

US 2013/0079314 A1 Mar. 28, 2013

Related U.S. Application Data

(62) Division of application No. 12/840,122, filed on Jul. 20, 2010, which is a division of application No. 11/815,428, filed as application No. PCT/JP2006/323095 on Nov. 20, 2006, now abandoned.

(30) Foreign Application Priority Data

Nov. 25, 2005 (JP) ................. 2005-340245

(51) Int. Cl.
*A61K 36/886* (2006.01)
(52) U.S. Cl.
USPC ........................................................ 424/744
(58) Field of Classification Search
None
See application file for complete search history.

(56) References Cited

U.S. PATENT DOCUMENTS

| 4,801,582 | A | 1/1989 | Hikino et al. |
| 5,929,051 | A | 7/1999 | Ni et al. |
| 2006/0088644 | A1 | 4/2006 | Choo et al. |

FOREIGN PATENT DOCUMENTS

| CA | 2 548 811 | 10/2005 |
| CA | 2 542 780 | 4/2006 |
| DE | 10 2004 041 612 A1 | 3/2005 |
| EP | 1 731 158 | 12/2006 |
| JP | 60-214741 | 10/1985 |
| JP | 8-165247 A | 6/1996 |
| JP | 08-208495 | 8/1996 |
| JP | 2832551 | 2/1998 |
| JP | 2000-319190 | 11/2000 |
| JP | 2002-068997 | 3/2002 |
| JP | 2002-205955 | 7/2002 |
| JP | 2002-284661 | 10/2002 |
| JP | 2003-113394 | 4/2003 |
| JP | 2003-286185 | 10/2003 |
| JP | 2005-068132 | 3/2005 |
| JP | 2005-087998 | 4/2005 |
| WO | WO 99/11144 | 3/1999 |
| WO | WO 2005/094838 A1 | 10/2005 |
| WO | WO 2006/035525 A1 | 4/2006 |

OTHER PUBLICATIONS

"All about solvents" web date: Apr. 27, 2012 [Retrieved from the Internet on: Mar. 1, 2013]. Retrieved from: <URL: http://www.masterorganicchemistry.com/2012/04/27/polar-protic-polar-aprotic-nonpolar-all-about-solvents/>.*
Bunyapraphatsara, et al. Antidiabetic Activity of *Aloe vera* L. Juice II. Clinical Trial in Diabetes Mellitus Patients in Combination with Glibenclamide, *Phytomedicine*, vol. 3, No. 3, pp. 245-248, 1996.
Okyar, et al. "Effect of *Aloe vera* Leaves on Blood Glucose Level in Type I and Type II Diabetic Rat Models," *Phytotherapy Research*, vol. 15, pp. 157-161, 2001.
Beppu, et al. "Hypoglycaemic and Antidiabetic Effects in Mice of *Aloe arborescens* Miller var *natalensis* Berger," *Phytotherapy Research*, vol. 7, pp. S37-S42, 1993.
Rajasekaran, et al. "Hypoglycemic Effect of *Aloe vera* Gel on Streptozotocin-Induced Diabetes in Experimental Rats," *Journal of Medicinal Food*, vol. 7, No. 1, pp. 61-66, 2004.
Yongchaiyudha, et al. "Antidiabetic Activity of *Aloe vera* L. Juice. I. Clinical Trial in New Cases of Diabetes Mellitus," *Phytomedicine*, vol. 3, No. 3, pp. 241-243, 1996.
Can, et al. "Effect of *Aloe vera* Leaf Gel and Pulp Extracts on the Liver in Type-II Diabetic Rat Models," *Biological 7 Pharmaceutical Bulletin (of Japan)*, vol. 27, No. 5, pp. 694-698, May 1, 2004.
Supplementary European Search Report dated Aug. 24, 2009.
Can, et al. "Effect of *Aloe vera* Leaf Gel and Pulp Extracts on the Liver in Type-II Diabetic Rat Models," *Biological & Pharmaceutical Bulletin (of Japan)*, vol. 27, No. 5. pp. 694-698, May 1, 2004.
European Search Report mailed May 18, 2010 issued to European patent application EP 10 15 7399.
Mohammad Najmul Ghani Khan; Khazaain-al-Advia vol. III (20$^{th}$ century AD), Nadeem Yunus Printer/Sheikh Mohd Basheer & Sons, Lahore, 1926, p. 631.

(Continued)

*Primary Examiner* — Amy L Clark
(74) *Attorney, Agent, or Firm* — Knobbe, Martens, Olson & Bear LLP

(57) ABSTRACT

An *Aloe vera* extract is provided that can be safely ingested and, can be used as a food material for treating lifestyle diseases such as hyperglycemia. The *Aloe vera* extract contains an extremely low level of an anthraquinone (anthraquinone-based compound), and can be added to foods. The *Aloe vera* extract is produced by a supercritical fluid extraction method and contains a mixture of a cyclolanostane compound and a lophenol compound in an amount of 1.0% by mass or more. The mass mixing ratio of cyclolanostane compound:lophenol compound is 5.1:4.9 to 6.3:2.7 and/or the content of an anthraquinone-based compound is 0.001% by mass or less.

3 Claims, No Drawings

(56) References Cited

OTHER PUBLICATIONS

Mohammad Azam Khan, Muheet-e-Azam vol. IV (Part I) (19$^{th}$ century AD) Matba Nizami, Kanpur. 1899, p. 175.

Govinda Dasa; Bhaisajya Ratnavali—edited by Rajeshvaradutta Shastri, translated by Ambikaduttashastri:Chaukhamba Sanskrit Sansthan, Varanasi, edn. 14$^{th}$, 2001 (This book contains back references from 1000 BC to 18$^{th}$ century), p. 808.

Siddhayogasamgrahah—Compiled by Yadavji Trikamji Acharya, Sri Baidyanath Ayurved Bhawan, Allahabad, edn. 1$^{st}$ 1978, pp. 156-157.

Kandasamy Mudaliar; Athmarakshaamirtham, Pub: Ilakkana Achagam, Chennai (1879), p. 576.

Kandasamy Mudaliar; Athmarakshaamirtham, Pub: Ilakkana Achagam, Chennai (1879), p. 584.

Communication from European Patent Office issued to application No. 06823482.2-2401 / 195287, dated Jun. 30, 2010 with Annexes 1-3.

Office Action dated Aug. 26, 2011 issued to European application No. 10 157 399.6.

Agasthiyar; Agathiar vaithiam 600. Pub & Ed. Anonymous, p. 8 (Jun. 25, 2010).

Hu et al., "Free radical-scavenging activity of *Aloe vera* (*Aloe barbadensis* Miller) extracts by supercritical carbon dioxide extraction," *Food Chemistry*, vol. 91, pp. 85-90 (2005).

Tanaka et al., "Identification of Five Phytosterols from *Aloe vera* Gel as Anti-diabetic Compounds," *Biol. Pharm. Bull.*, vol. 29(7), pp. 1418-1422 (2006).

\* cited by examiner

METHOD FOR TREATING HYPERGLYCEMIA

RELATED APPLICATIONS

This application is a divisional of U.S. application Ser. No. 12/840,122, filed. Jul. 20, 2010, which is a divisional of U.S. application Ser. No. 11/815,428, filed Aug. 2, 2007, which is the U.S. National Phase under 35 U.S.C. §371 of International Application PCT/JP2006/323095, filed Nov. 20, 2006, which was published in a non-English language, which claims priority to JP Application No. 2005-340245, filed Nov. 25, 2005. The disclosures of the above-described applications are hereby incorporated by reference in their entirety.

TECHNICAL FIELD

The present invention relates to an *Aloe vera* extract containing a mixture that consists of a cyclolanostane compound and a lophenol compound in an amount of 1.0% by mass or more, a method of producing the *Aloe vera* extract by a supercritical fluid extraction method, and a hyperglycemia improving agent containing, as an active ingredient, an *Aloe vera* extract containing a mixture that consists of a cyclolanostane compound and a lophenol compound in an amount of 1.0% by mass or more.

BACKGROUND ART

It is known that a worsened hyperglycemic state causes various diseases, and the state is referred to as diabetes. In Japan, it is said that there are more than sixteen millions of patients in the prediabetic state (so-called borderline patients), and in view of the current lifestyle habits, the number of the patients is expected to continue to increase in the future. In order to prevent development of diabetes caused by the hyperglycemic state, blood glucose levels must be controlled in the long term.

The hyperglycemic state is a state where blood glucose levels are beyond the normal range, and the normal range is a state of a fasting blood glucose level: 110 mg/dl or less, a blood glucose level one hour after loading of 75 g of sugar: 160 mg/dl, and a blood glucose level two hour after loading of 75 g of sugar: 120 mg/dl or less (Non-Patent Document 1).

Hemoglobin A1c, a binding substance of glucose and hemoglobin, increases depending on the degree of hyperglycemia. Because hemoglobin A1c once produced does not disappear until the life span of erythrocyte (120 days) ends, it reflects the past blood glucose control conditions over a long period of time (Non-patent document 1).

Further, α-glucosidase inhibitors, sulfonylurea drugs as insulin secretagogues, thiazolidine derivatives as insulin resistance improving agents and the like are currently used as therapeutic agents for diabetes. However, the drug efficacies thereof are not satisfactory, and they suffer many problems such as side effects causing coma due to rapid drop in blood glucose level. Meanwhile, as a drug including a naturally-derived ingredient having an effect of suppressing an increase in a blood glucose level, the prior art references have disclosed a hyperglycemia suppressing agent containing a banaba-derived ingredient (Patent document 1), a hyperglycemia suppressing agent containing a concentrated extract of fermentation product of wheats or barleys as an active ingredient (Patent document 2) and the like.

Phytosterols are broadly classified into three groups: 4-desmethylsterols; 4-monomethylsterols; and 4,4-dimethylsterols. Examples of 4-desmethylsterols include generally widely known cholesterol, campesterol, brassicasterol, sitosterol, stigmasterol, and fucosterol, examples of 4-monomethylsterols include lophenol and foliol, and examples of 4,4-dimethylsterols include cycloartanol and lupeol.

As methods of producing those phytosterols, there have been disclosed a method of collecting phytosterols with methanol from rape oil and soybean oil, and a method that includes immersing crude phytosterols in an organic solvent and separating the organic solvent to separate β-sitosterol, stigmasterol, campesterol, and brassicasterol (Patent Document 3).

There have been disclosed methods of producing 4,4-dimethylsterols, which include: a method of producing cycloartenol and 24-methylenecycloartanol (which is a conventional name of 24-methylene-9,19-cyclolanostan-3-ol) (Patent Document 4); and a method of producing cycloartenol ferulate from γ-oryzanol and a method of synthesizing a compound using a hydrolysate thereof as a starting substance (Patent Document 5). However, a method of producing 4-monomethylsterols, in particular, a compound having a lophenol skeleton has been unknown.

As a techniques for isolating phytosterols by a supercritical fluid extraction method, a one- and two-stage supercritical fluid extraction technique for concentrates of carotene, vitamin E, and other minor ingredients has been disclosed. For example, there have been disclosed a method of extracting phytosterols (campesterol, stigmasterol, β-sitosterol) in natural fat and oil (Patent Document 6), a method of producing phytosterols in the *Amorphophallus konjac* by a supercritical fluid extraction method, and a hypocholesterolemic agent, a prostatic hypertrophy improving agent, and a food or drink including the same (patent Document 7), and the like.

The genus *Aloe* in the family Liliaceae is a group of plants including *Aloe vera* (*Aloe barbadensis* Miller) and *Aloe arborescens* (*Aloe arborescens* Miller var. *natalensis* Berger), and the like, and they are empirically known to have various efficacies. The prior arts regarding a blood glucose level improving effect of those efficacies of plants of the genus *Aloe* include: clinical studies in the United States (Non-Patent Document 2); a hypoglycemic action observed in animal studies (Non-Patent Documents 3 or 4); and a hypoglycemic action of polysaccharides in plants of the genus *Aloe* (Patent document 8). Moreover, an *Aloe vera* squeezed liquid and a hypoglycemic agent containing the squeezed liquid as an active ingredient (Patent Document 9) have been disclosed.

Meanwhile, as techniques for extracting an active ingredient in *Aloe* having a blood glucose level improving effect, the following techniques have been disclosed. For example, the techniques include: a method of producing an *Aloe vera* gel stock solution, which includes sterilization with chlorine, superheating at 90° C., and filtration (Patent Document 10); a method of producing an *Aloe vera* gel squeezed liquid which is characterized in that all steps are carried out at 75° C. or lower (Patent Document 11); an *Aloe vera* squeezed liquid obtained by squeezing and filtration steps and by a treatment using activated carbon, diatom earth, and a sterilization filter, while controlling heating to 60° C. for 30 minutes in all production steps (Patent Document 12); and a method of producing *Aloe* products which includes preparing an *Aloe* juice from leaves of an *Aloe* plant; adjusting the pH of the juice to 3 to 3.5; precipitating activated substances by adding a water-soluble lower aliphatic polar solvent to form a heterogeneous solution; and removing the water-soluble lower aliphatic polar solvent and solubilized substances to isolate the precipitated activated substances (Patent Document 13).

Also disclosed are a technique for producing an extract having an immunodepression-improving effect by: ultracentrifuging *Aloe vera*; collecting an ethanol-dissolved part of the resultant supernatant; and performing distribution extraction of the fraction with butanol (Patent Document 14) and a technique for producing a prophylactic and improving agent for obesity by performing distribution extraction of an aqueous solution of an *Aloe* squeezed liquid or solvent extract with ethyl acetate or butanol (Patent Document 15)

Patent Document 1: JP 2003-95941 A
Patent Document 2: JP 2002-371003 A
Patent Document 3: JP 2002-542161 A
Patent Document 4: JP 57-018617 A
Patent Document 5: JP 2003-277269 A
Patent Document 6: JP 2005-87998 A
Patent Document 7: JP 2003-113394 A
Patent Document 8: JP 60-214741 A
Patent Document 9: JP 2003-286185 A
Patent Document 10: JP 2002-68997 A
Patent Document 11: JP 2002-284661 A
Patent Document 12: JP 2002-205955 A
Patent Document 13: JP 2832551 B
Patent Document 14: JP 08-208495 A
Patent Document 15: JP 2000-319190 A
Non-Patent Document 1: Nippon Rinsho, No. 808, Vol. 2, pp. 405-409, 2002
Non-Patent Document 2: Phytomedicine, Vol. 3, pp. 245-248, 1996
Non-Patent Document 3: Phytotherapy Research, Vol. 15, pp. 157-161, 2001
Non-Patent Document 4: Phytotherapy Research, Vol. 7, pp. 37-42, 1993

DISCLOSURE OF THE INVENTION

In development of a functional food using a plant such as *Aloe*, the plant must be used in consideration of the water content thereof. For example, in *Aloe vera* gel (mesophyll part of *Aloe vera*), the water content is about 98% or more, and a major part of the solid part is composed of polysaccharides. Therefore, applicable forms of foods were considerably restricted because of physical problems. Moreover, there was a problem that the contents of non-active ingredients of *Aloe vera* gel must be considered to determine the intake amount for ensuring its functionality.

As described in Patent Documents 8 to 10 above, techniques for producing a food that contains *Aloe vera* gel excluding an anthraquinone (anthraquinone-based compound) in *Aloe vera* gel have been studied, but emphasis is on excluding unwanted ingredients. Therefore, only those techniques have not solved a problem of providing a production method that includes efficiently extracting a target active ingredient without containing unwanted ingredients.

Meanwhile, Patent Documents 6 or 7 above discloses a method of extracting phytosterols by a supercritical fluid extraction method, but does not describe and suggest a method of efficiently collecting phytosterols having hyperglycemia improving effects and yielding an extract containing no anthraquinone, and such an extract.

That is, there has not been known a technique for producing an *Aloe vera* extract without using an organic solvent, which is intended to be applied to foods and includes easily and efficiently separating phytosterols and anthraquinones in *Aloe vera*.

In view of the above-described objects, the inventors of the present invention have extensive studies to obtain a form (composition) of *Aloe vera*, which is suitable for exerting the activity sufficiently as a material of a functional food and for addition to foods. Moreover, the inventors of the present invention have used an *Aloe vera* squeezed liquid (or a dry powder thereof) as a material to carry out purification by a supercritical fluid extraction method, and as a result, they obtained an extract containing a cyclolanostane compound and a lophenol compound and having a composition broadly reflecting the mix ratio of phytosterols in natural *Aloe vera*, and found that the extract contains almost no anthraquinones and has an significant hyperglycemia improving effect, thus completing the present invention.

The present invention is intended to provide an *Aloe vera* extract that can be safely ingested, can be used as a material of a food for preventing lifestyle diseases, contains an extremely low level of an anthraquinone, can be added to foods, and contains phytosterols (including a cyclolanostane compound and a lophenol compound); and a method of producing the *Aloe vera* extract.

Another object of the present invention is to provide a hyperglycemia improving agent containing the *Aloe vera* extract as an active ingredient.

The first invention of the present application to solve the above-described problems relates to an *Aloe vera* extract containing a mixture that consists of a cyclolanostane compound and a lophenol compound in an amount of 1.0% by mass or more, in which the extract has the following properties (1) and/or (2):

(1) the mass mixing ratio of the cyclolanostane compound and lophenol compound is as follows:
cyclolanostane compound:lophenol compound=6.3:2.7 to 5.1:4.9; and/or (2) the content of an anthraquinone-based compound is 0.001% by mass or less.

Hereinafter, the *Aloe vera* extract is also referred to as "*Aloe vera* extract of the present invention".

A preferred aspect of the first invention of the present application is the following (3) and/or (4):

(3) the cyclolanostane compound is 9,19-cyclolanostan-3-ol and/or 24-methylene-9,19-cyclolanostan-3-ol; and/or (4) the lophenol compound is one or plural compounds selected from 4-methyloholest-7-en-3-ol, 4-methylergost-7-en-3-ol, and 4-methylstigmast-7-en-3-ol.

The second invention of the present application to solve the above-described problems relates to food or drink containing the *Aloe vera* extract of the first invention of the present application.

A preferred aspect of the *Aloe vera* extract in the food or drink of the present invention relates to the same as that of the first invention of the present application. Meanwhile, a preferred content of the *Aloe vera* extract in the food or drink is 0.01% by mass or more.

The third invention of the present application to solve the above-described problems relates to a method of producing an *Aloe vera* extract including: preparing powdery *Aloe vera* mesophyll by removing water from a mesophyll part excluding leaf skin of *Aloe vera* by freeze-drying or hot-air drying; and extracting an *Aloe vera* extract from the resultant powdery *Aloe vera* mesophyll by a supercritical fluid extraction method based on the following conditions (a) to (e):

(a) the extraction solvent is carbon dioxide;
(b) the extraction temperature is 50 to 69° C.;
(c) the pressure is 15 to 60 MPa;
(d) no entrainer is used; and
(e) the extraction time is 50 to 70 minutes.

The fourth invention of the present application to solve the above-described problems relates to a hyperglycemia improving agent including, as an active ingredient, an *Aloe* vera extract containing a mixture that consists of a cyclolanostane compound and a lophenol compound in an amount of 1.0% by mass or more, in which the *Aloe vera* extract has the following properties (5) and/or (6):

(5) the mass mixing ratio of the cyclolanostane compound and lophenol compound is as follows:

cyclolanostane compound:lophenol compound=6.3:2.7 to 5.1:4.9; and/or (6) the content of an anthraquinone-based compound is 0.001% by mass or less.

A preferred aspect of the fourth invention of the present application is the following (7) and/or (8):

(7) the cyclolanostane compound is 9,19-cyclolanostan-3-ol and/or 24-methylene-9,19-cyclolanostan-3-ol; and/or (8) the lophenol compound is one or plural compounds selected from 4-methylcholest-7-en-3-ol, 4-methylergost-7-en-3-ol, and 4-methylstigmast-7-en-3-ol.

The fifth invention of the present application to solve the above-described problems relates to a use of an *Aloe vera* extract containing a mixture that consists of a cyclolanostane compound and a lophenol compound in an amount of 1.0% by mass or more for producing a hyperglycemia improving agent, in which the *Aloe vera* extract has the following properties (9) and/or (10):

(9) the mass mixing ratio of the cyclolanostane compound and lophenol compound is as follows:

cyclolanostane compound:lophenol compound=6.3:2.7 to 5.1:4.9; and/or

(10) the content of an anthraquinone-based compound is 0.001% by mass or less.

Note that a preferred aspect of the fifth invention of the present application is the following (11) and/or (12):

(11) the cyclolanostane compound is 9,19-cyclolanostan-3-ol and/or 24-methylene-9,19-cyclolanostan-3-ol; and/or

(12) the lophenol compound is one or plural compounds selected from 4-methylcholest-7-en-3-ol, 4-methylergost-7-en-3-ol, and 4-methylstigmast-7-en-3-ol.

The sixth invention of the present application to solve the above-described problems relates to a method characterized by administering an *Aloe vera* extract containing a mixture that consists of a cyclolanostane compound and a lophenol compound in an amount of 1.0% by mass or more for improving hyperglycemia to a subject whose hyperglycemia is to be improved, in which the *Aloe vera* extract has the following properties (13) and/or (14):

(13) the mass mixing ratio of the cyclolanostane compound and lophenol compound is as follows:

cyclolanostane compound:lophenol compound=6.3:2.7 to 5.1:4.9; and/or

(14) the content of an anthraquinone-based compound is 0.001% by mass or less.

An *Aloe vera* extract of the present invention is safe, has a significant hyperglycemia improving effect, and is applicable as a material of a functional food, in particular, a food for specified health use. Meanwhile, the content of an anthraquinone (anthraquinone-based compound) is low, so that the extract can be ingested as a food. In addition, an *Aloe vera* extract of the present invention does not contain a substance improper as an additive for foods such as an organic solvent, and therefore can be applied to all foods.

In addition, a production method provided by the present invention can provide a material suitable for development of a functional food using *Aloe vera* and promote application of *Aloe vera* to foods.

BEST MODE FOR CARRYING OUT THE INVENTION

Hereinafter, preferred embodiments of the present invention will be described in detail. However, the present invention is not limited to the following preferred embodiments and can be modified freely within the scope of the present invention. Note that, in the present description, percentages are by mass unless otherwise specified.

In an *Aloe vera* extract of the present invention, the content of a mixture consisting a cyclolanostane compound and a lophenol compound is 1.0% by mass or more, preferably 1.2% by mass or more, further preferably 2.0% by mass or more.

The cyclolanostane compound is a compound represented by the following Formula (1) (a compound having a cyclolanostane skeleton).

[Chem. 1]

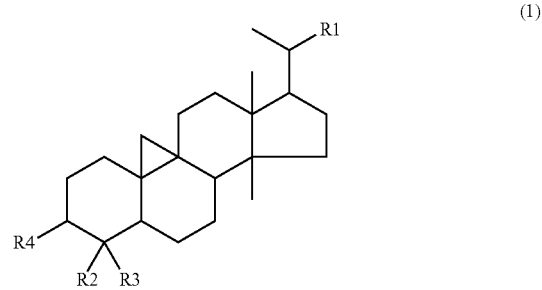

In Formula (1), R1 represents an alkyl group or an alkenyl group including one or two double bonds, which is straight or branched chain having 6 to 8 carbon atoms, or a substituted alkyl or alkenyl group obtained by substituting one or two hydrogen atoms in the above-described alkyl and alkenyl groups for a hydroxyl group and/or a carbonyl group; R2 and R3 each independently represent a hydrogen atom or a methyl group; and R4 forms C=O with a carbon atom constituting a ring or represents any one of the following formulae

[Chem. 2]

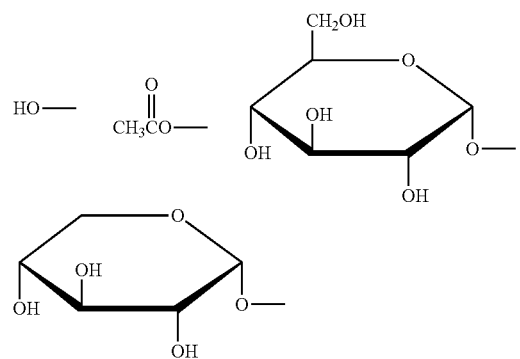

In Formula (1) above, R1 is preferably any one of the groups represented by the following formulae.

—$CH_2$—$CH_2$—$CH_2$—$CH(CH_3)_2$

—$CH_2$—$CH_2$—$CHRa$-$C(CH_3)_2Rb$  [Chem. 3]

(wherein Ra is a hydrogen atom, a hydroxyl group, or a methyl group; and Rb is a hydrogen atom or a hydroxyl group)

—$CH_2$—$CH_2$—$CH(CH_2CH_3)$—$CH(CH_3)_2$

—$CH_2$—$CH_2$—$CHRc$-$C(CH_3)$=$CH_2$ (wherein Rc is a hydrogen atom, a hydroxyl group, or a methyl group)

—CH$_2$—CH$_2$—C(=O)—C(CH$_3$)=CH$_2$

—CH$_2$—CH$_2$—C(=CH$_2$)—CH(CH$_3$)$_2$

—CH$_2$—CH$_2$—CH=C(CH$_3$)$_2$

—CH$_2$—CH=C(CH$_3$)—CH(CH$_3$)$_2$

—CH$_2$—CH$_2$—C(=CHCH$_3$)—CH(CH$_3$)$_2$

Meanwhile, the lophenol compound is a compound represented by the following Formula (2) (a compound having a lophenol skeleton).

[Chem. 4]

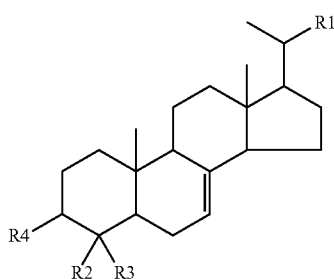

(2)

In Formula (2), R1 represents an alkyl group or an alkenyl group including one or two double bonds, which is straight or branched chain having 5 to 16 carbon atoms. The alkyl or alkenyl group may be a substituted alkyl or alkenyl group obtained by substituting at least one hydrogen atom for a hydroxyl group and/or a carbonyl group. R2 and R3 each independently represents a hydrogen atom, an alkyl group or a substituted alkyl group having 1 to 3 carbon atoms; and R4 forms C=O with a carbon atom constituting a ring or represents —OH or —OCOCH$_3$. The alkyl group having 1 to 3 carbon atoms is preferably a methyl group, an ethyl group, etc., particularly preferably a methyl group.

In Formula (2) above, R1 is preferably any one of the groups represented by the following formulae.

—CH$_2$—CH$_2$—CH(—CH$_2$—CH$_3$)—CH(CH$_3$)$_2$

—CH$_2$—CH$_2$—CH=C(CH$_3$)$_2$

—CH$_2$—CH=C(CH$_3$)—CH(CH$_3$)$_2$

—CH$_2$—CH$_2$—C(=CH—CH$_3$)—CH(CH$_3$)$_2$

—CH$_2$—CH$_2$—CH(Ra)=C(CH$_3$)Rb    [Chem. 5]

(wherein Ra and Rb are any of —H, —OH, or —CH$_3$)

—CH$_2$—CH$_2$—CH(Rc)—CH(CH$_3$)Rd (wherein Rc and Rd are any of —H, —OH, or —CH$_3$)

Meanwhile, the mass mixing ratio of a cyclolanostane compound and a lophenol compound in a phytosterol in an *Aloe vera* extract of the present invention is preferably within the range of cyclolanostane compound:lophenol compound=6.3:2.7 to 5.1:4.9; more preferably within the range of cyclolanostane compound:lophenol compound=6.3:3.7 to 5.5:4.5.

Moreover, the cyclolanostane compound is preferably 9,19-cyclolanostan-3-ol (represented by Formula (3) below) and/or 24-methylene-9,19-cyclolanostan-3-ol (represented by Formula (4) below), and the lophenol compound is preferably one or plural compounds selected from 4-methylcholest-7-en-3-ol (represented by Formula (5) below), 4-methylergost-7-en-3-ol (represented by Formula (6) below), and 4-methylstigmast-7-en-3-ol (represented by Formula (7) below)

[Chem. 6]

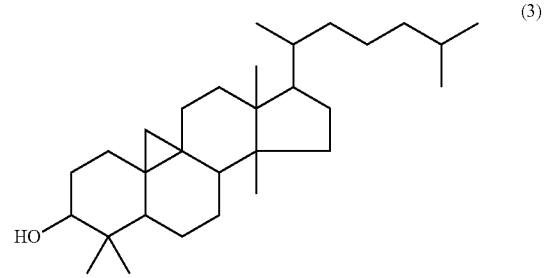

(3)

[Chem. 7]

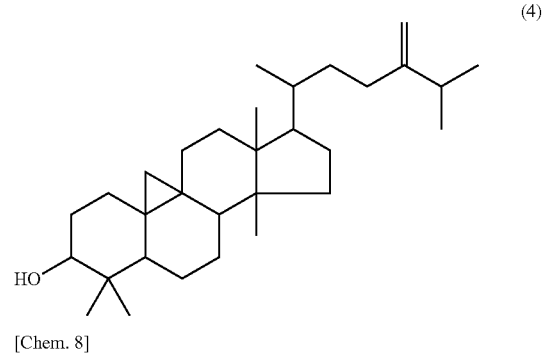

(4)

[Chem. 8]

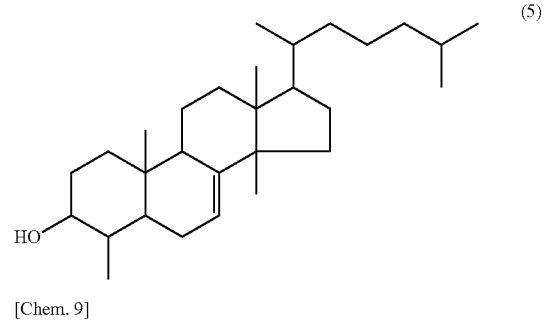

(5)

[Chem. 9]

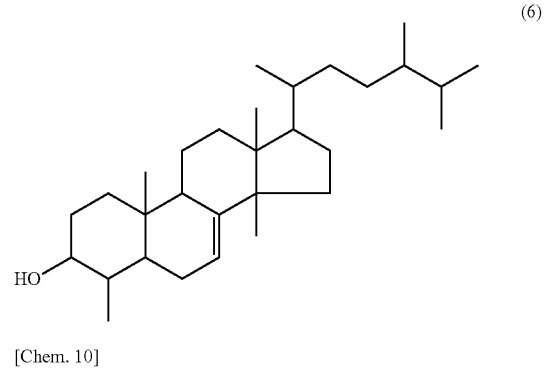

(6)

[Chem. 10]

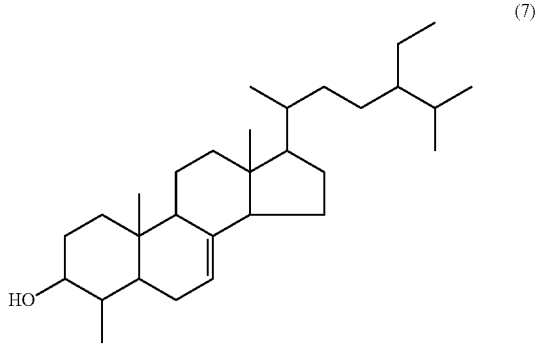

(7)

Meanwhile, an *Aloe vera* extract of the present invention may contain an anthraquinone-based compound such as aloenin, barbaloin, or aloe-emodin (in the present invention, sometimes referred to as "anthraquinone") in an amount that does not cause practical problems, but the contents of those compounds are preferably small because they have laxative effects.

In particular, an *Aloe vera* extract of the present invention contains aloenin or barbaloin in an amount of preferably 0.001% by mass or less, further preferably 0.0003% by mass or less, or particularly preferably, the extract does not contain aloenin or barbaloin. Meanwhile, an *Aloe vera* extract of the present invention contains aloe-emodin in an amount of preferably 0.001% by mass or less, further preferably 0.0003% by mass or less, most preferably 0.00028% by mass or less.

An *Aloe vera* extract of the present invention can be produced from a starting material, *Aloe vera* (*Aloe barbadensis Miller*) belonging to the genus *Aloe* in the family Liliaceae, by the following method. An extract in the same matter as the *Aloe vera* extract of the present invention can be produced as follows: a succulent plant such as *Aloe arborescens* (*Aloe arborescen Miller* var. *natalensis Berger*) is used as a starting material in the same way as the method of the present invention, to thereby produce an *Aloe arborescens* extract or the like.

For example, if a leaf of *Aloe vera* is laterally sliced, the epidermic external wall covered with thick cuticle emerges. Mesophyll differentiated into green tissue cells and thin cells of cell wall, known as parenchyma, is located below the epidermis. The parenchyma cells contain transparent mucilage-like jelly. A bundle having internal bundle sheath cells contains yellow liquid juice having properties of a laxative and is located be two big cells. *Aloe vera* has two kinds of main liquid sources yellow latex (exudate) and transparent gel (mucilage). In particular, transparent gel (mucilage) from parenchyma cells of the plant is referred to as *Aloe vera* gel. As described above, a leaf of *Aloe vera* includes three different parts (1) yellow liquid juice, mainly an anthraquinone (anthraquinone-based compound); (2) internal gel matrix or "mesophyll"; and (3) "skin (leaf skin)" including exodermis, top, base, and pricks, An *Aloe vera* extract of the present invention is preferably produced by the supercritical fluid extraction method. Specifically, the extract is produced by: preparing powdery *Aloe vera* mesophyll from a mesophyll part excluding leaf skin of *Aloe vera* by freeze-drying or hot-air drying; and subjecting the resultant powdery *Aloe vera* mesophyll to a supercritical fluid extraction method based on the following conditions (a) to (e):
(a) the extraction solvent is carbon dioxide;
(b) the extraction temperature is 50 to 69° C.;
(c) the pressure is 15 to 60 MPa;
(d) no entrainer is used; and
(e) the extraction time is 50 to 70 minutes.

From the viewpoint of improving extraction efficiency of cyclolanostane compounds and lophenol compounds, supercritical propane, supercritical ethylene, supercritical 1,1,1,2-tetrafluoroethane, etc may be used as the extraction solvent, but from the viewpoint of improving safety as food or drink, carbon dioxide is preferably used. The extraction temperature may be appropriately selected from a temperature range of 28° C. to 120° C., but in order to improve extraction efficacy of cyclolanostane compounds and lophenol compounds and decrease the content of an anthraquinone-based compound (such as aloe-emodin), the temperature is preferably within a range of 50 to 69° C., further preferably within a range of 50 to 59° C. Meanwhile, the pressure may be appropriately selected from a range of 5.5 to 60 MPa, but in order to improve extraction efficacy of cyclolanostane compounds and lophenol compounds and decrease the content of an anthraquinone-based compound, the pressure is preferably within a range of 15 to 60 MPa, further preferably within a range of 15 to 24 MPa. In addition, in the present invention, from the viewpoint of improving extraction efficacy of cyclolanostane compounds and lophenol compounds, an entrainer such as ethanol may be used, but from the viewpoint of decreasing the content of an anthraquinone-based compound, it is preferable not to use an entrainer.

An *Aloe vera* extract of the present invention has an effect of lowering a hemoglobin A1c level, and as a result, it can control a blood glucose level for a long period of time. Therefore, an *Aloe vera* extract of the present invention may be used as an active ingredient of a hyperglycemia improving agent.

The contents of a cyclolanostane compound, a lophenol compound, and an anthraquinone-based compound in a hyperglycemia improving agent of the present invention are the same as those in an *Aloe vera* extract of the present invention.

Meanwhile, an *Aloe vera* extract of the present invention may be used as an active ingredient of a drug or food or drink for improving hyperglycemia.

A drug for improving hyperglycemia including an *Aloe vera* extract of the present invention (hereinafter, also referred to as "drug of the present invention") may be an *Aloe vera* extract of the present invention itself or the like, or may be produced using the *Aloe vera* extract or the like in combination with a pharmaceutically acceptable pharmaceutical carrier, and may be administered orally or parenterally to a mammal including a human. In a drug of the present invention, a cyclolanostane compound and/or a lophenol compound in an *Aloe vera* extract may be pharmaceutically acceptable salts. The pharmaceutically acceptable salts include both of metallic salts (inorganic salts) and organic salts, and a list of the salts is shown in "Remington's Pharmaceutical Sciences, 17th ed., pp. 1418, 1985". Specifically, examples thereof include, but not limited to, inorganic acid salts such as hydrochlorides, sulfates, phosphates, diphosphates, and hydrobromides, and organic acid salts such as malates, maleates, fumarates, tartrates, succinates, citrates, acetates, lactates, methanesulfonates, p-toluenesulfonates, pamoates, salicylates, and stearates. Meanwhile, the pharmaceutically acceptable salts may be salts of a metal such as sodium, potassium, calcium, magnesium, or aluminum, or salts of an amino acid such as lysine. In addition, the present invention includes a drug containing a solvate such as a hydrate of a cyclolanostane compound and/or a lophenol compound in an *Aloe vera* extract or a pharmaceutically acceptable salt thereof.

Dosage form of the drug of the present invention is not particularly limited and can be suitable selected depending on the therapeutic purpose. Specific examples thereof include tablet, pill, powder, solution, suspension, emulsion, granules, capsule, syrup, suppository, injection, ointment, patch, eye drop, nasal drop and so forth. For the preparation, additives generally used in usual hyperglycemia improving drugs as pharmaceutical carriers such as excipients, binders, disintegrating agents, lubricants, stabilizers, flavoring agents, diluents, surfactants and solvents for injection can be used. Furthermore, so long as the effect of the present invention is not degraded, the *Aloe vera* extract of the present invention can be used in combination with other drugs having a hyperglycemia improving effect.

Although the amount of the *Aloe vera* extract of the present invention contained in the drug of the present invention is not particularly limited and can be suitably selected, the amount in the pharmaceutical preparation may be, for example, 0.001 to 10% by mass, preferably 0.01 to 1% by mass, in terms of the amount of the mixture which consists of a cyclolanostane compound and a lophenol compound.

The drug of the present invention is useful for a therapeutic or prophylactic treatment of a disease resulted from hyperglycemic conditions such as diabetes and its associated symptoms and conditions (likelihood of developing diabetes or related conditions). In particular, it can also be used to prevent onset of diabetes mellitus from hyperglycemic conditions. Furthermore, the drug of the present invention can cure or prevent various diseases, complications and so forth resulted from hyperglycemic conditions, and reduce risks of these diseases, complications and so forth. Examples of such various diseases and complications resulted from hyperglycemic conditions include diabetic retinopathy, diabetic nephropathy, diabetic neuropathy, diabetic gangrene, cerebral apoplexy resulted from diabetes mellitus, myocardial infarction resulted from diabetes mellitus and so forth.

The term "hyperglycemic conditions" refers to conditions that the blood glucose levels are out of the normal ranges, and the normal ranges are generally defined as a fasting blood glucose level of 110 mg/dl or lower, a blood glucose level of 160 mg/dl or lower 1 hour after 75 g glucose load, and a blood glucose level of 120 mg/dl or lower 2 hours after the same glucose load (Nihon Rinsho, No. 806, Vol. 1, pp. 28-35, 2002). Furthermore, the drug of the present invention is preferably used for a treatment for a patient with a hemoglobin A1c level higher than normal, for example, a hemoglobin A1c level of 5.8% or higher The administration time of the drug of the present invention is not particularly limited and can be suitably selected according to the method for treating an objective disease. Furthermore, the administration route is preferably determined depending on the dosage form, age, sex and other conditions of patients, severity of symptoms of patients and so forth. The dose of the active ingredient in the drug of the present invention is suitably selected depending on the dosing regimen, age, sex, severity of disease, other conditions of patients and so forth. The amount of the mixture which consists of a cyclolanostane compound and a lophenol compound is usually selected from the range of, preferably 0.001 to 50 mg/kg/day, more preferably 0.01 to 1 mg/kg/day, as a tentative dose. Furthermore, the dry weight of the *Aloe vera* extract the present invention is selected from the range of, preferably 0.1 to 1000 mg/kg/day, more preferably to 100 mg/kg/day, as a tentative amount. The drug of the present invention can be ingested, in a day, once or several times as divided portions.

An *Aloe vera* extract of the present invention or the like may be contained in food or drink. The food or drink is not particularly limited as long as the effect of the above-described active ingredient is not diminished. Meanwhile, the *Aloe vera* extract content in food or drink of the present invention is not particularly limited as long as the effect of the above-described active ingredient is obtained, but it is preferably 0.01 to 50% by mass, particularly preferably 0.01 to 20% by mass. In addition, food or drink of the present invention can be produced by a general method using a material to be used for general food or drink except that the above-described active ingredient is added thereto.

The food or drink of the present invention can be used for various applications utilizing the hyperglycemia improving effect. For example, it can be used for applications as food or drink suitable for those who are getting concerned about their blood glucose levels, food or drink useful for decreasing or eliminating risk factors of lifestyle-related diseases such as diabetes mellitus, and so forth.

As for the food or drink of the present invention, the expression "improvement of hyperglycemia" means that improvement or prevention of various health damages resulted from hyperglycemia, and as other actions and effects of the food or drink of the present invention, "prevention of hyperglycemia," "suppression of increase in blood glucose level," "improvement of increase in blood glucose level," "prevention of increase in blood glucose level" and so forth are exemplified in the present invention as terms having a meaning similar to that of the aforementioned "improvement of hyperglycemia".

Furthermore, the food or drink of the present invention is useful for a treatment or a prevention of a disease resulted from hyperglycemic conditions such as diabetes and its associated symptoms and conditions (likelihood of developing diabetes or related conditions). In particular, it can also be used to prevent onset of diabetes from hyperglycemic conditions. Furthermore, the food or drink of the present invention can be used for a prophylactic treatment of various diseases, complications and so forth resulted from hyperglycemic conditions and can decrease risks of these diseases, complications and so forth.

Examples of such various diseases and complications resulted from hyperglycemic conditions include diabetic retinopathy, diabetic nephropathy, diabetic neuropathy, diabetic gangrane, cerebral apoplexy resulted from diabetes mellitus, myocardial infarction resulted from diabetes mellitus and so forth.

The food or drink of the present invention is preferably marketed as food or drink attached with an indication that the food or drink is used for improving hyperglycemia, for example, "food or drink containing a compound having hyperglycemia improving effect indicated as 'For improving hyperglycemia,'" "food or drink containing a plant extract indicated as 'For improving hyperglycemia,'" and so forth. Because the *Aloe vera* extract of the present invention have a hyperglycemia improving effect, it is considered that the indication of "improvement of hyperglycemia" also means "suppression of increase in blood glucose level." Therefore, the food or drink of the present invention can be indicated as "For suppressing increase in blood glucose level." That is, the aforementioned indication of "For improvement of hyperglycemia" may be an indication of "For suppression of increase in blood glucose level."

The wording used for such an indication as mentioned above is not necessarily be limited to the expression "For improvement of hyperglycemia" or "For suppression of increase in blood glucose level", and any other wording expressing the effect of improving hyperglycemia or suppressing increase in blood glucose level of course falls within the scope of the present invention. As such a wording, for example, an indication based on various uses allowing consumers to recognize the effect of improving hyperglycemia or suppressing increase in blood glucose level is also possible. Examples include, for example, indications of "Suitable for those who are getting concerned with blood glucose levels", "Useful for decrease or elimination of risk factors (risks) of lifestyle-related diseases such as diabetes mellitus", and so forth.

The aforementioned term "indication" include all actions for informing consumers the aforementioned use, and any indications reminding or analogizing the aforementioned use fall within the scope of the "indication" of the present invention regardless of purpose, content, objective article, medium etc. of the indication. However, the indication is preferably made with an expression that allows consumers to directly recognize the aforementioned use. Specific examples include actions of indicating the aforementioned use on goods or packages of goods relating to the food or drink of the present invention, actions of assigning, delivering, displaying for the purpose of assigning or delivering or importing such goods or packages of goods indicated with the aforementioned use, displaying or distributing advertisements, price lists or business papers relating the goods with indicating the aforementioned use, or providing information including those as contents with indicating the aforementioned use by an electromagnetic method (Internet etc.) and so forth.

The indication is preferably an indication approved by the administration etc. (for example, an indication in a form based on an approval, which is qualified on the basis of any of various legal systems provided by the administration), and it is particularly preferably an indication on advertisement materials at the sales spots such as packages, containers, catalogs, pamphlets and POPS, others documents and so forth.

Examples of the indication further include, for example, indications as health food, functional food, enteric nutritive food, food for special dietary uses, food with nutrient function claims, quasi-drug and so forth as well as indications approved by the Ministry of Health, Labor and Welfare, for example, indications approved on the basis of the system of food for specified health uses and similar systems. Examples of the latter include indications as food for specified health uses, indications as food for specified health uses with qualified health claims, indications of influence on body structures and functions, indications of reduction of disease risk claims and so forth, and more precisely, typical examples include indications as food for specified health uses (especially indications of use for health) provided in the enforcement regulations of Health Promotion Law (Japan Ministry of Health, Labor and Welfare, Ministerial ordinance No. 86, Apr. 30, 2003) and similar indications.

Hereinafter, the present invention will be described in detail by way of Test Examples.

Test Example 1

This test was carried out to examine compositions of *Aloe vera* extracts extracted by different methods.
(1) Sample Preparation
(a) Preparation of *Aloe vera* Extract by Supercritical Fluid Extraction Method For 60 kg of *Aloe vera*, leaf skins were peeled, and mesophyll parts were collected. The collected mesophyll parts were freeze-dried to thereby prepare 300 g of *Aloe vera* mesophyll powder. Subsequently, extraction was carried out for 20 g of the resultant *Aloe vera* mesophyll powder by a supercritical fluid extraction method. The supercritical fluid extraction was carried out using $CO_2$ delivery pump (SCF-GET), PU-2080 pump (PU-2080 plus), and Back Pressure Regulator (SCF-BPG), manufactured by JASCO Corporation, and a blunger manufactured by TOYO KOATSU Co, Ltd., and using carbon dioxide as an extraction solvent, based on the supercritical extraction conditions 1 to 8 described in Table 1, and the *Aloe vera* extracts obtained under the supercritical extraction conditions were named extracts 1 to 8.

TABLE 1

| Supercritical extraction condition | Extraction temperature (°C.) | Pressure (MPa) | Extraction time (minute) | Entrainer (ml/min: when used) |
|---|---|---|---|---|
| 1 | 50 | 15 | 60 | None |
| 2 | 50 | 15 | 60 | Ethanol (0.5) |
| 3 | 50 | 25 | 60 | None |
| 4 | 50 | 15 | 60 | Ethanol (0.25) |
| 5 | 70 | 15 | 60 | Ethanol (0.25) |
| 6 | 70 | 15 | 60 | None |
| 7 | 70 | 25 | 60 | None |
| 8 | 50 | 15 | 120 | None |

(b) Preparation of *Aloe vera* Extract by Organic Solvent Extraction Method

To 100 g of *Aloe vera* gel was added 2 L of a mix solution including chloroform and methanol in equal amounts, and the mixture was subjected to extraction with stirring at room temperature for two hours. Filtration was carried out using filter paper to remove insoluble fractions, to thereby obtain an extraction solution, and then the solvents (chloroform and methanol) were removed by an evaporator to prepare an *Aloe vera* extract (extract 9)

(2) Test Method

For the extracts 1 to 9 the contents of cyclolanostane compounds, 9,19-cyclolanostan-3-ol and 24-methylene-9,19-cyclolanostan-3-ol; lophenol compounds, 4-methylcholest-7-en-3-ol, 4-methylergost-7-en-3-ol, and 4-methylstigmast-7-en-3-ol; and an anthraquinone (anthraquinone-based compound), aloe-emodin were measured by LC-MS (manufactured by Shimadzu Corporation) using brassicasterol (manufactured by Wako Pure Chemical Industries, Ltd.) as an internal standard substance.

(3) Test Results

The results of this test are shown in Table 2. In Table 2, the respective symbols represent the following compounds. S: Total extraction amount of *Aloe vera* extract. (mg), A: cyclolanostane compound (mixture of two kinds of compounds), A-1: 9,19-cyclolanostan-3-ol, 24-methylene-9,19-cyclolanostan-3-ol, B: lophenol compound (mixture of three kinds of compounds), B-1: 4-methylcholest-7-en-3-ol, B-2: 4-methylergost-7-en-3-ol, B-3: 4-methylstigmast-7-en-3-ol, aloe-emodin The total extraction amount of an *Aloe vera* extract in the case of preparing the extract by the organic solvent extraction method was found to be larger than that in the case of preparing the extract by the supercritical fluid extraction method. On the other hand, the rate of the content of the mixture of a cyclolanostane compound and a lophenol compound in an *Aloe vera* extract prepared by the supercritical fluid extraction method was found to be generally higher (10-fold or more) than that in an *Aloe vera* extract prepared by the organic solvent extraction method.

Meanwhile, the contents of anthraquinones, which are considered to be unpreferable as additives for foods, were determined. The results revealed that aloenin and barbaloin were not detected in the respective extracts, but aloe-emodin was only slightly detected and remained in the *Aloe vera* extracts in different amounts depending on the extraction methods or extraction conditions. In particular, it was clarified that the extraction condition 1 in the supercritical fluid extraction method (extraction was carried out without using an entrainer under conditions of extraction temperature: 50° C., extraction pressure 15 MPa, extraction time 60 minutes) can remove aloe-emodin with the utmost efficiency.

TABLE 2

| Extract | S (mg) | (A + B)/S (%) | A/(A + B) (%) | A-1/(A + B) (%) | A-2/(A + B) (%) | B/(A + B) (%) | B-1/(A + B) (%) | B-2/(A + B) (%) | B-3/(A + B) (%) | E/S (%) |
|---|---|---|---|---|---|---|---|---|---|---|
| 1 | 33.0 | 1.26 | 60.42 | 34.59 | 25.83 | 39.57 | 14.39 | 12.47 | 12.71 | 0.00028 |
| 2 | 45.0 | 1.02 | 59.22 | 32.68 | 26.54 | 40.78 | 15.22 | 13.52 | 12.04 | 0.00413 |
| 3 | 41.5 | 1.53 | 62.05 | 35.20 | 26.85 | 37.96 | 14.57 | 11.91 | 11.48 | 0.00241 |
| 4 | 68.0 | 1.16 | 63.73 | 35.37 | 28.36 | 36.26 | 14.52 | 11.32 | 10.42 | 0.00348 |
| 5 | 85.0 | 1.03 | 73.22 | 41.06 | 32.16 | 26.78 | 12.13 | 9.65 | 5.00 | 0.00594 |
| 6 | 27.5 | 1.90 | 67.32 | 34.89 | 32.43 | 32.69 | 12.77 | 11.98 | 7.94 | 0.00160 |
| 7 | 41.0 | 0.74 | 51.97 | 28.75 | 23.22 | 48.03 | 13.79 | 14.82 | 19.42 | 0.00190 |
| 8 | 25.0 | 2.31 | 66.83 | 37.57 | 29.26 | 33.18 | 14.87 | 11.00 | 7.31 | 0.00652 |
| 9 | 97.6 | 0.08 | 61.07 | — | — | 38.93 | — | — | — | 0.01383 |

※S, A, A-1, A-2, B, B-1, B-2, B-3, and E in the table represent the following terms.
S: Total extraction amount of Aloe vera extract
A: Cyclolanostane compound (mixture of two kinds of compounds)
A-1: 9,19-cyclolanostan-3-ol
A-2: 24-methylene-9,19-cyclolanostan-3-ol
B: lophenol compound (mixture of three kinds of compounds)
B-1: 4-methylcholest-7-en-3-ol
B-2: 4-methylergost-7-en-3-ol
B-3: 4-methylstigmast-7-en-3-ol
E: aloe-emodin Test Example 2

This test was carried out to examine hyperglycemia improving effects of *Aloe vera* extracts of the present invention.
(1) Sample Preparation The concentrations of *Aloe vera* extracts prepared under the same conditions as the supercritical fluid extraction condition 1 in the supercritical fluid extraction method in Test Example 1 above were adjusted to 77 µg/ml (1 µg/ml in terms of the concentration of the mixture consisting of a cyclolanostane compound and a lophenol compound) with an aqueous DMSO solution, to thereby prepare test samples, In this step, final DMSO concentrations were adjusted to 0.2% with physiological saline. Meanwhile, an *Aloe vera* squeezed liquids obtained by peeling leaf skins of *Aloe vera*, collecting mesophyll parts, crushing the collected mesophyll part using a juicer mixer, and removing fibrous precipitates was used as a control sample. Note that an aqueous solution of 0.2% DMSO was used as a negative sample.
(2) Test Method As model mice of Type II diabetes, 6-week-old male db/db mice (purchased from Clea Japan, Inc.) were used and divided into groups including seven mice per group. The test samples, control sample, and negative sample (1 ml each) were orally administered to each group once a day using a sonde over 34 days every day. 35 days after the start of administration, hemoglobin A1c was measured using DCA2000 (manufactured by Bayer-Sankyo Co., Ltd.)
(3) Test Results The results of this test are shown in Table 3. The results revealed that the hemoglobin A1c levels in the mice administered with test samples were decreased by 30% or more relative to the negative sample administered group, and the test sample was found to have activities for improving hyperglycemia. Herein, in the *Aloe vera* squeezed liquids having the same solid contents as those of the test samples, decreases in the hemoglobin A1c levels were not observed at all. Therefore, in the case where the hypoglycemic effects (hyperglycemia improving effects) were considered as indicators, the *Aloe vera* extracts of the present invention (supercritical fluid extracts) have the effects 13,000-fold higher than those of the *Aloe vera* squeezed liquids, which were calculated from their effective doses. Furthermore, in the mice administered with the test samples, pathological side effects were not observed at all

TABLE 3

| Sample | Blood hemoglobin A1c relative value (%) | p value |
|---|---|---|
| Test sample | 69.4 ± 6.2 | 0.0001* |
| Control sample | 82.1 ± 0.1 | 0.01* |
| Negative sample | 100 | |

*This symbol represents that the value is statistically significant.

Hereinafter, the present invention will be described in more detail by way of Examples, but is not limited to the following Examples.

Example 1

Production of *Aloe vera* Extract

For 60 kg of *Aloe vera*, leaf skins were peeled, and mesophyll (transparent gel) parts were collected. The collected mesophyll parts were freeze-dried, to thereby prepare 300 g of *Aloe vera* mesophyll powder.

Extraction was carried out for 20 g of the resultant *Aloe vera* mesophyll powder by the supercritical fluid extraction method. The supercritical fluid extraction was carried out using $CO_2$ delivery pump (SCF-GET), PU-2080 pump (PU-2080 plus), and Back Pressure Regulator (SCF-BPG), manufactured by JASCO Corporation, and a blunger manufactured by TOYO KOATSU Co., Ltd., and using carbon dioxide as an extraction solvent under conditions of extraction temperature: 50° C., extraction pressure: 15 MPa, and extraction time: 60 minutes without using an entrainer. As a result, 33 mg of *Aloe vera* extract was produced.

For the resultant *Aloe vera* extracts, the compositions were analyzed by LC-MS. The results revealed that: the extracts contained cyclolanostane compounds, 9,19-cyclolanostan-3-ol and 24-methylene-9,19-cyclolanostan-3-ol, and lophenol compounds, 4-methylcholest-7-en-3-ol; 4-methylergost-7-en-3-ol, and 4-methylstigmast-7-en-3-ol; and the ratios of 9,19-cyclolanostan-3-ol, 24-methylene-9,19-cyclolanostan-3-ol, 4-methylcholest-7-en-3-ol, 4-methylergost-7-en-3-ol, and 4-methylstigmast-7-en-3-ol were 0.437% by mass, 0.326% by mass, 0.182% by mass, 0.158% by mass, and 0.161% by mass, respectively.

Note that hyperglycemia improving effects of the above-described *Aloe vera* extracts were measured in the same way as Test Example 2, and as a result, the effects of lowering hemoglobin A1c levels were confirmed.

Example 2

A tablet drug having the following composition and having a hyperglycemia improving effect was produced by the following method
*Aloe vera* extract produced in Example 1 (dry product) 40(%)
Lactose (manufactured by Morinaga Milk Industry Co., Ltd.) 18.5 Corn starch (manufactured by Nisshin Seifun Group Inc.) 30.7 Magnesium stearate (manufactured by Taihei Chemical Industrial Co., Ltd.) 1.4
Carboxymethylcellulose calcium (Gotoku Chemical Company Co., Ltd.) 9.4
A mixture of an *Aloe vera* extract (dry product), lactate, corn starch, and carboxymethylcellulose calcium was uniformly kneaded while appropriately adding sterile purified water, and the mixture was dried at 50° C. for 3 hours. Magnesium stearate was added to the resultant dry product, and the mixture was mixed, followed by making tablet in accordance with a conventional method, to thereby yield a tablet containing a mixture of a cyclolanostane compound and a lophenol compound in an amount of about 0.5% by mass.

Example 3

10.8 kg of an enzymatically degraded product of whey protein (manufactured by Morinaga Milk Industry Co., Ltd.), 36 kg of dextrin (manufactured by Showa Sangyo Co., Ltd.), and small amounts of a water-soluble vitamin and a mineral were dissolved in 200 kg of water to prepare an aqueous phase in a tank. On the other hand, 3 kg of soybean cooking oil (manufactured by Taiyo-yushi Co. Ltd.), 8.5 kg of palm oil (manufactured by Taiyo-yushi Co. Ltd.), 2.5 kg of safflower oil (manufactured by Taiyo-yushi Co. Ltd.), 0.2 kg of lecithin (manufactured by Ajinomoto Co., Inc.), 0.2 kg of fatty acid monoglyceride (manufactured by Kao Corporation), and a small amount of a fat-soluble vitamin were mixed and dissolved to prepare an oil phase. The oil phase was added to the aqueous phase in the tank and mixed by stirring, and the mixture was heated to 70° C., followed by homogenization using a homogenizer at a pressure of 14.7 MPa. Subsequently, the homogenate was sterilized at 90° C. for 10 minutes and then concentrated, followed by spray-drying, to thereby prepare about 59 kg of intermediate product powder. To 50 kg of the resultant intermediate product powder were added 6.8 kg of sucrose (manufactured by Hokuren), 167 g of amino acid mix powder (manufactured by Ajinomoto Co., Inc.), and 600 g of the *Aloe vera* extract (dry product) produced in Example 1, and the mixture was uniformly mixed, to thereby produce about 57 kg of enteral food powder that contains the *Aloe vera* extract (dry product) in an amount of about 0.01% by mass and has a hyperglycemia improving effect.

Example 4

A solution (120 kg) containing the *Aloe vera* extract in an amount of about 0.05% by mass in an aqueous solution of Ryoto Polygly Ester (manufactured by Mitsubishi-Kagaku Foods Corporation) (concentration 1,000 ppm) was prepared, and 160 g of anhydrous citric acid (manufactured by Wako Pure Chemical Industries, Ltd.), 6 g of sucralose (manufactured by San-Ei Gen F.F.I., Inc.), and 1 g of Sunett (registered trademark: manufactured by Nutrinova) as an artificial sweetener were mixed and dissolved in the solution. Moreover, 79.821 kg of water was added, and finally, 12 g of a flavor (manufactured by T. Hasegawa Co., Ltd.) was added, to thereby prepare a mix solution. The resultant mix solution was filtrated using a filter with a mesh size of 20, and the filtrate was sterilized at 96° C.±1° C. for 30 seconds and filled into 125-ml cartocan containers, to thereby produce about 950 *Aloe vera* gel drinks that contains the *Aloe vera* extract in an amount of 0.03% by mass and has a hyperglycemia improving effect.

INDUSTRIAL APPLICABILITY

An *Aloe vera* extract of the present invention is safe, has a significant hyperglycemia improving effect, is applicable as a material of a functional food, in particular, food for specified health use, has a low content of a compound of an anthraquinone (anthraquinone-based compound), can be ingested as food, and can be applied to all foods. In addition, a production method provided by the present invention can provide a material suitable for development of a functional food using *Aloe vera* and promote application of *Aloe vera* to foods.

What is claimed is:

1. A method for treating hyperglycemia in a subject in need thereof comprising administering to said subject an effective amount of purified *Aloe vera* mesophyll supercritical carbon dioxide extract, wherein said purified *Aloe vera* mesophyll supercritical carbon dioxide extract comprises a mixture consisting of one or more cyclolanostane compound(s) and one or more lophenol compound(s), wherein the mixture is present in an amount of 1.0% by mass or more, and wherein the purified *Aloe vera* mesophyll supercritical carbon dioxide extract has the following properties (1) and/or (2):
   (1) the purified *Aloe vera* mesophyll supercritical carbon dioxide extract has a mass mixing ratio of the one or more cyclolanostane compound(s) and one or more lophenol compound(s) and wherein the mass mixing ratio is: cyclolanostane compound(s):lophenol compound(s)=5.1:4.9 to 6.3:2.7; and/or
   (2) the purified *Aloe vera* mesophyll supercritical carbon dioxide extract has anthraquinone-based compound(s) in an amount of 0.001% by mass or less.

2. The method of claim 1, wherein the one or more cyclolanostane compound(s) are selected from the group consisting of 9,19-cyclolanostan-3-ol and/or 24-methylene-9,19-cyclolanostan-3-ol.

3. The method of claim 1, wherein the one or more lophenol compound(s) are selected from the group consisting of 4-methylcholest-7-en-3-ol, 4-methylergost-7-en-3-ol and/or 4-methylstigmast-7-en-3-ol.

* * * * *